United States Patent [19]

Yonemitsu et al.

[11] 4,013,725
[45] Mar. 22, 1977

[54] PROCESS FOR PREPARING HYDROPEROXIDE

[75] Inventors: Eiichi Yonemitsu, Kashiwa; Takeo Igarashi, Nagareyama; Naoto Osaki; Tetsuo Aoyama, both of Tokyo; Yukiya Nakazato, Matsudo, all of Japan

[73] Assignee: Mitsubishi Gas Chemical Company, Inc., Tokyo, Japan

[22] Filed: May 6, 1975

[21] Appl. No.: 574,898

[30] Foreign Application Priority Data

May 14, 1974 Japan .............................. 49-53570
May 14, 1974 Japan .............................. 49-53571

[52] U.S. Cl. ..................... 260/610 B; 260/621 C
[51] Int. Cl.² .............. C07C 179/02; C07C 179/04
[58] Field of Search ........ 260/610 B, 610 A, 621 C

[56] References Cited

UNITED STATES PATENTS

| | | | |
|---|---|---|---|
| 2,663,740 | 12/1953 | Calhoun et al. | 260/610 B |
| 2,906,789 | 8/1959 | McNaughton | 260/674 |
| 2,950,237 | 8/1960 | Sharp | 204/158 |
| 3,816,540 | 6/1974 | Barne | 260/610 B |

*Primary Examiner*—James O. Thomas, Jr.
*Assistant Examiner*—W. B. Lone
*Attorney, Agent, or Firm*—Brooks Haidt Haffner and Delahunty

[57] ABSTRACT

A process for preparing hydroperoxide by autoxidizing secondary alkyl group-substituted methylbenzenes in the presence of water comprises using as a catalyst a water-soluble chelate compound in which multidentate ligands are coordinated to at least one member selected from the class of cobalt, nickel, manganese, copper and iron.

14 Claims, No Drawings

PROCESS FOR PREPARING HYDROPEROXIDE

BACKGROUND OF THE INVENTION

1. Field of the Invention

This invention relates to a process for preparing a hydroperoxide, more particularly it relates to a process for preparing a hydroperoxide by autoxidizing secondary alkyl group-substituted methylbenzenes.

2. Description of the Prior Art

Hydroperoxide prepared by autoxidizing secondary alkyl group-substituted methylbenzenes is useful as a starting material for preparing an alkyl-substituted phenol, particularly a methyl-substituted phenol. Secondary alkyl-group-substituted methylbenzenes, for example 3,5-dimethyl-isopropylbenzen (3,5-dimethyl cumene) is autoxidized to give the tertiary hydroperoxide and primary hydroperoxide as illustrated below.

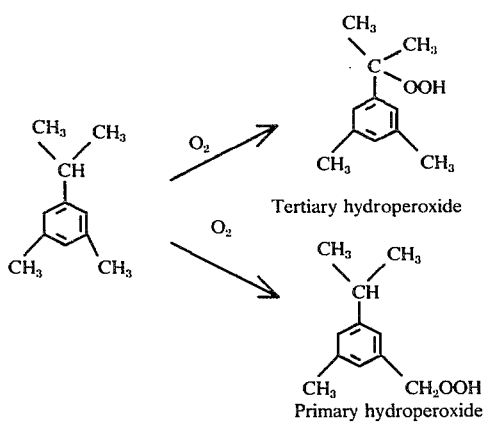

The tertiary hydroperoxide is subjected to acid decomposition reaction to obtain a methyl substituted phenol, for example, 3,5-xylenol, and the primary hydroperoxide undergoes decomposition to give a methyl secondary alkyl phenol for example, 3-methyl-5-isopropylphenol.

It has been heretofore well known that tertiary hydroperoxide is prepared by autoxidizing secondary alkyl group-substituted benzenes, for example isopropylbenzene (cumene) and it is obtained in high yield and high selectivity. However, in case of secondary alkyl group-substituted methylbenzenes, they are remarkable low in the oxidation rate and very poor in the selectivity as compared with secondary alkyl group-substituted benzenes. Such tendency of the secondary alkyl group-substituted methylbenzenes becomes remarkable as the number of the methyl group increases. On account of this, a hydroperoxide has not been obtained from secondary alkyl group-substituted methylbenzenes, at a high efficiency. In order to eliminate such drawback, it has been demanded to develop a process for preparing a hydroperoxide from the above-mentioned methylbenzenes at a higher oxidation rate and a higher selectivity.

SUMMARY OF THE INVENTION

It is a primary object of this invention to provide a process for preparing a hydroperoxide by autoxidizing secondary alkyl group-substituted methylbenzenes which is free from the foregoing drawback.

It is another object of this invention to provide a process for preparing a hydroperoxide by autoxidizing secondary alkyl group-substituted methylbenzenes in which the oxidation of the methylbenzenes proceeds at a high rate.

It is a still further object of this invention to provide a process for preparing a hydroperoxide by autoxidizing secondary alkyl group-substituted methylbenzenes in which the hydroperoxide is obtained at a high oxidation rate, a high selectivity and a high yield.

It is a still further object of this invention to provide a process for preparing a hydroperoxide by autoxidizing secondary alkyl group-substituted methylbenzenes in which a catalyst capable of being semipermanently repeatedly used is employed.

It is a still further object of this invention to provide a process for preparing a hydroperoxide by autoxidizing secondary alkyl group-substituted methylbenzenes which is advantageously applicable to a continuous process.

According to this invention, there is provided a process for preparing hydroperoxide by autoxidizing secondary alkyl group-substituted methylbenzenes in the presence of water which comprises using as a catalyst a water-soluble chelate compound in which multidentate ligands are coordinated to at least one metal selected from the class of cobalt, nickel, manganese, copper and iron.

DESCRIPTION OF THE PREFERRED EMBODIMENTS

The methylbenzenes to be used in this invention are those having a secondary alkyl group-substituent. As examples thereof, there may be mentioned a secondary alkyl toluene such as isopropyltoluene, isobutyltoluene, diisopropyltoluene and the like, a secondary alkyl xylene such as isopropylxylene, isobutylxylene, diisopropylxylene and the like, a secondary alkyl trimethylbenzene such as isopropyltrimethylbenzene and the like and a secondary alkyl tetramethylbenzene such as isopropyltetramethylbenzene and the like. Among these secondary alkyl group-substituted methylbenzenes, the secondary alkyl xylene particularly, isopropylxylene is preferable.

The catalyst to be used in this invention for the purpose of accelerating the reaction rate of the secondary alkyl group-substituted methylbenzenes is a metal chelate compound. More particularly, it is a metal chelate compound in which two or more multidentate ligands are coordinated to at least one metal selected from the class of cobalt, nickel, manganese, copper and iron and which is soluble in water. Among these metals, cobalt is preferable. As the multidentate ligand, there may be mentioned nitrogen containing polycarboxylic acids such as ethylenediaminetetraacetic acid, cyclohexanediaminetetraacetic acid, nitrilotriacetic acid and the like, and polyphosphoric acids and the like. Among them, nitrogen containing polycarboxylic acids, particularly ethylenediaminetetraacetic acid is preferable. The catalyst may be used singly or in combination and is dissolved in water for use thereof. The amount of the catalyst may be selected depending on various conditions, and it is generally 3 parts or less by weight, preferably 0.001 to 1 part per 100 parts of the secondary alkyl group-substituted methylbenzene which is starting material.

The water to be used in this invention may be used in an amount ranging from 0.01 to 20 parts, preferably 0.1 to 2 parts per one part of the secondary alkyl group-substituted methylbenzene.

As described above, a chelate compound in which ethylene diaminetetraacetic acid is coordinated to cobalt is particularly preferable as the catalyst to be used in this invention. When the above-mentioned chelate compound is used as the catalyst, it is preferable to adjust the pH value of the aqueous solution in the reaction system to that ranging from about 5 to 7.5, more preferably about 5.5 to 7.0 so that the catalyst can be used in a smaller amount ad repeatedly used. Further, when the oxidation reaction is carried out under such condition, the oxidation rate and the selectivity of the resulting hydroperoxide become higher. Furthermore, the stability of the catalyst is remarkably improved so that it becomes possible to use the catalyst semipermanently repeatedly because the activity thereof is not deteriorated. In this case, if the pH value is larger than 7.5, precipitate is liable to form in the reaction solution so that the activity of the catalyst is deteriorated. If the pH value is smaller than 5, the oxidation rate of the secondary alkyl group-substituted methylbenzene becomes slow, which is inadvantageous especially in a continuous process. The adjustment of the pH value is effected at the time of the reaction by adding successively an alkali. As such alkali, carbonates, bicarbonates and carboxylates of sodium and potassium are preferable. Among the carboxylates are included sodium salt and potassium salt of an aliphatic carboxylic acid, sodium salt and potassium salt of an aromatic carboxylic acid and the like.

The process according to this invention can be conducted both in a batch process and continuous process. Particularly, in case of the continuous process, the effect of this invention is extremely remarkable.

As the oxidizing agent, an oxygen-containing gas, for example oxygen, air and the like are used. The reaction may be carried out at a temperature ranging from 50° to 130° C, preferably 80° to 110° C. Where the reaction temperature is too high, the resulting hydroperoxide is liable to self-decompose due to the heat so that the by-product increases. The reaction pressure may be more than atmospheric pressure, particularly preferable the range of from atmospheric pressure to 50 kg/cm² gauge.

After the reaction is completed, the reaction solution is recovered from the reactor and separated into an oil phase and water phase. The resulting hydroperoxide is contained in the oil phase. The water phase contains the catalyst and can be used cyclically.

In this invention, a hydroperoxide can be obtained from secondary alkyl group-substituted methylbenzenes at a high reaction rate, a high yield and a high selectivity. Consequently, a highly concentrated hydroperoxide solution can be obtained in a short time.

In this invention, the catalyst is long in its life, usable semipermanently and hardly soluble in the oil phase, and therefore it can be advantageously used cyclically. The process of this invention is applicable particularly to a continuous process for preparing a hydroperoxide.

Further, in this invention, the use of any emulsifier is not necessarily required. When emulsifier is not used, the reaction solution can be more easily separated.

The invention will be understood more readily by reference to the following examples, however these examples are intended to illustrate the invention and are not to be construed to limit the scope of the invention.

In the Examples, parts are by weight unless otherwise specified.

EXAMPLE 1

In a pressure-resistant reactor equipped with a stirrer were placed 100 parts of 3,5-dimethyl cumene, 0.5 part of disodium cobalt ethylenediaminetetraacetate, 100 parts of water and 1.0 part of cumene hydroperoxide and the mixture was vigorously stirred at a temperature of 110° C under a pressure of 5.0 kg/cm² gauge for two hours while blowing oxygen into the reactor. After the completion of the reaction, the reaction solution was separated into an oil phase and water phase. It was found that the concentration of the total hydroperoxide contained in the oil phase was 9.0% by weight and the selectivity of the total hydroperoxide to the converted dimethyl cumene was 92.5 mole %.

EXAMPLE 2

In the same reactor as that used in Example 1 were placed 100 parts of 3,5-dimethyl cumene, 0.2 parts of disodium cobalt ethylenediaminetetraacetate, 50 parts of water and 1.0 part of cumene hydroperoxide and the mixture was vigorously stirred at 110° C and under 5.0 kg/cm² gauge for three hours while blowing air into the reactor. It was found that the concentration of the total hydroperoxide contained in the oil phase after the completion of the reaction was 5.8% by weight and the selectivity of the total hydroperoxide to the converted dimethyl cumene was 93.1 mole %.

EXAMPLE 3

In the reactor used in Example 1 were placed 100 parts of 3,5-dimethyl cumene, 0.5 parts of disodium manganese ethylenediaminetetraacetate, 100 parts of water and 1.0 part of cumene hydroperoxide, and the mixture was vigorously stirred under 5.0 kg/cm² gauge at 110° C for four hours with blowing air into the reactor. It was found that the concentration of the total hydroperoxide contained in the oil phase after the completion of the reaction was 7.6% by weight and the selectivity of the hydroperoxide to the converted dimethyl cumene was 91.0 mole %.

EXAMPLE 4

In the same reactor as that used in Example 1 were placed 100 parts of 3,5-dimethyl cumene, 0.5 parts of disodium manganese ethylenediaminetetraacetate, 100 parts of water and 1.0 part of cumene hydroperoxide, the mixture of which was vigorously stirred under a pressure of 5.0 kg/cm² gauge at 100° C for four hours while blowing air into the reactor. It was found that the concentration of the total hydroperoxide contained in the oil phase after the completion of the reaction was 4.3% by weight and the selectivity of the total hydroperoxide to the converted dimethyl cumene was 90.2 mole %.

EXAMPLE 5

In the same reactor as in Example 1 were placed 100 parts of 3,5-dimethyl cumene, 0.7 parts of disodium nickel ethylenediaminetetraacetate, 50 parts of water and 1.0 part of cumene hydroperoxide, the mixture of which was vigorously stirred under a pressure of 5.0 kg/cm² gauge at 110° C for four hours while blowing air into the reactor. The concentration of the total hydroperoxide contained in the oil phase after the completion of the reaction was found to be 5.4% by weight and the selectivity of the total hydroperoxide to the converted dimethyl cumene was found to be 91.7 mole %.

EXAMPLE 6

In the same reactor as that in Example 1 were placed 100 parts of 3,5-dimethyl cumene, 0.6 parts of disodium copper ethylenediaminetetraacetate, 50 parts of water and 1.0 part of cumene hydroperoxide, the mixture of which was vigorously stirred under a pressure of 5.0 kg/cm$^2$ gauge at 110° C for 4 hours while blowing air into the reactor. It was found that the concentration of the total hydroperoxide contained in the oil phase after the completion of the reaction was 5.1 % by weight and the selectivity of the total hydroperoxide to the converted dimethyl cumene was 92.3 mole %.

EXAMPLE 7

In the same reactor as that used in Example 1 were placed 100 parts of 3,5-dimethyl cumene, 0.7 parts of disodium iron ethylenediaminetetraacetate, 50 pats of water and 1.0 part of cumene hydroperoxide and the mixture was vigorously stirred under a pressure of 5.0 kg/cm$^2$ gauge at 110° for 4 hours while blowing air into the reactor. It was found that the total hydroperoxide was contained in the oil phase at the completion of the reaction in a concentration of 5.2 % by weight and the selectivity of the total hydroperoxide to the converted dimethyl cumene was 92.1 mole %.

EXAMPLE 8

In the same reactor as used in Example 1 were charged 100 parts of 3,5-dimethyl cumene, 0.5 parts of disodium cobalt cyclohexanediaminetetraacetate, 100 parts of water and 1.0 part of cumene hydroperoxide to carry out the reaction at 110° C under 5 kg/cm$^2$ gauge for three hours while blowing air into the reactor. The concentration of the total hydroperoxide contained in the oil phase after the completion of the reaction was 9.2% by weight and the selectivity of the total hydroperoxide to the converted dimethyl cumene was 90.3 mole %.

EXAMPLE 9

The same procedure as in Example 8 was repeated except that 0.5 parts of sodium cobalt nitrilotriacetate was used in place of the disodium cobalt cyclohexane diaminetetraacetate and the reaction time was controlled so as to be four hours. As the result, it was found that the concentration of the total hydroperoxide contained in the oil phase was 2.7% by weight and the selectivity was 93.5 mole %.

Comparison Example

A comparison test was made in the same manner as that in Example 1 except that no catalyst was used and the pressure was controlled so as to be 10 kg/cm$^2$ gauge. As the result of the test, it was found that the concentration of the total hydroperoxide contained in the oil phase of the reaction solution after the completion of the reaction was only 1.3% by weight.

EXAMPLE 10

In to a pressure-resistant reactor for continuous oxidation equipped with a stirrer were continuously charged 3.5-dimethyl cumene at a rate of 530 part/hour and a 0.1% by weight aqueous solution of disodium cobalt ethylenediaminetetraacetate at a rate of 350 parts/hour to carry out the reaction under a pressure of 5 kg/cm$^2$ gauge at a temperature of 100° C while blowing air at a rate of 40N m$^3$/hour into the reactor. At that time, a 1% by weight aqueous solution of sodium bicarbonate was added so as to adjust th pH value of the aqueous solution to 7.0. The residence time of the 3,5-dimethyl cumene in the reaction system was 3 hours.

It was found that the concentration of the total hydroperoxide in the oil phase under the equilibrium state was 6.9% by weight. In the total hydroperoxide, the ratio of the tertiary hydroperoxide to the primary hydroperoxide was 72.2 : 27.8, and the selectivity of the total hydroperoxide to the converted 3,5-dimethyl cumene was 93.5 mole %.

EXAMPLE 11

In to the same reactor as that used in Example 10 were continuously charged 3,5-dimethyl cumene at a rate of 530 parts/hour and a 0.1% by weight aqueous solution of disodium cobalt ethylenediaminetetraacetate at a rate of 330 parts/hour, and while air was blown at a rate of 40N m$^3$/hour, a 1% by weight aqueous solution of sodium carbonate was additionally supplied so as to adjust the pH value of the aqueous solution in the reaction system. The reaction was conducted under such a condition that the pressure was 2.0 kg/cm$^3$ gauge, the temperature 100° C and the residence time of the 3,5-dimethyl cumene three hours.

As the result of the reaction, it was found that the concentration of the total hydroperoxide in the oil phase under the equilibrium state was 8.4% by weight and that the ratio of the tertiary hydroperoxide to the primary hydroperoxide was 73.3 : 26.7 and the selectivity of the total hydroperoxide to the converted 3,5-dimethyl cumene was 93.6 mole %.

Reference Experiment

Into the same reactor as that used in Example 10 were charged 3,5-dimethyl cumene at a rate of 550 parts/hour, disodium cobalt ethylenediaminetetraacetate at a rate of 0.74 parts/hour and water at a rate of 350 parts/hour to carry out the reaction under such a condition that the pressure was 5.0 kg/cm$^2$ gauge, the temperature 100° C and the residence time three hours while blowing air at a rate of 40N m$^3$/hour.

When equilibrium is reached, the concentration of the total hydroperoxide in the oil phase was only 4.3% by weight and the pH value of the aqueous solution in the reactor was 4.3 – 4.5.

The reaction mixture was taken out from the reactor and separated into an oil phase and water phase. The water phase was reused to carry out the same reaction as mentioned above. That is, the water phase and 3,5-dimethyl cumene were charged at a rate of 350 parts/hour and 550 parts/hour, respectively into the reactor and air was blown at a rate of 40N m$^3$/hour. As the result, it was found that the concentration of the total hydroperoxide in the oil phase under the equilibrium state was only 1.8% by weight.

EXAMPLE 12

The aqueous solution which had been separated after the completion of the reaction in Example 10 and 3,5-dimethyl cumene were charged at rates of 350 parts/hour and 530 parts/hour, respectively into the reactor, and further a 1% aqueous solution of sodium bicarbonate was supplied so as to adjust the pH value of the aqueous solution in the reactor to 6.5. The reaction is caused to take place under such a condition that the pressure was 5.0 kg/cm$^2$ gauge, the temperature 90° C and the residence time three hours while blowing air at a rate of 40N m³/hour.

The concentration of the total hydroperoxide in the oil phase under the equilibrium state was 8.2% by weight. In addition, the ratio of the tertiary hydroperoxide to the primary hydroperoxide was 74.2 : 25.8 and the selectivity of the total hydroperoxide to the converted 3,5-dimethyl cumene was 92.2 mole %.

EXAMPLE 13

Into the same reactor as in Example 10 were charged 3,5-dimethyl cumene and a 0.1% by weight aqueous solution of disodium cobalt ethylenediaminetetraacetate at rates of 250 parts/hour and 120 parts/hour, respectively, and air was introduced at a rate of 40N m³/hour to carry out the reaction at 100° C under 5.0 kg/ch² gauge with stirring. At that time, a 1.0% by weight aqueous solution of sodium bicarbonate was successfully supplied in order that the pH value of the aqueous solution might be about 5.6. The residence time of the 3,5-dimethyl cumene in the reactor was about 7 hours.

The concentration of the total hydroperoxide in the oil phase when equilibrium was reached was 11.6% by weight. The ratio of the tertiary hydroperoxide to the primary hydroperoxide was 74.7 : 25.3 and the selectivity of the total hydroperoxide to the converted 3,5-dimethyl cumene was 91.0 mole %.

We claim:

1. A process for preparing hydroperoxide by autoxidizing secondary alkyl group-substituted methylbenzenes, wherein the secondary alkyl group is isopropyl or isobutyl, with oxygen-containing gas in the presence of water at a pressure of about atmospheric up to about 50 kg/cm² gauge and at a temperature of from 50° to 130° C which comprises using as a catalyst a water-soluble chelate compound in which nitrogen containing polycarboxylic acid is selected from the group consisting of ethylene diamine tetraacetic acid, cyclohexane diamine tetraacetic acid, and nitrilotriacetic acid, and is coordinated to at least one metal selected from the class of cobalt, nickel, manganese, copper, and iron.

2. A process for preparing hydroperoxide according to claim 1, in which the nitrogen containing polycarboxylic acid is ethylenediaminetetraacetic acid.

3. A process for preparing hydroperoxide according to claim 1, in which the metal is cobalt.

4. A process for preparing hydroperoxide according to claim 1, in which the chelate compound is that wherein ethylenediaminetetraacetic acid is coordinated to cobalt.

5. A process for preparing hydroperoxide according to claim 4, in which the aqueous solution in the reaction system is adjusted to a pH value ranging from 5 to 7.5 by adding an alkali.

6. A process for preparing hydroperoxide according to claim 4, in which the aqueous solution in the reaction system is adjusted to a pH value ranging from 5.5 to 7.0 by adding an alkali.

7. A process for preparing hydroperoxide according to claim 5, in which the alkali is at least one member selected from the class of carbonates, bicarbonates and carboxylates of sodium and potassium.

8. A process for preparing hydroperoxide according to claim 1, in which the secondary alkyl group-substituted methylbenzene is at least one member selected from the class of secondary alkyl toluene, secondary alkyl xylene, secondary alkyl trimethylbenzene and secondary alkyl tetramethylbenzene.

9. A process for preparing hydroperoxide according to claim 8, in which the secondary alkyl group-substituted methylbenzene is a xylene.

10. A process for preparing hydroperoxide according to claim 8, in which the secondary alkyl group-substituted methylbenzene is at least one member selected from the class of isopropyl xylene, isobutyl xylene and diisopropyl xylene.

11. A process for preparing hydroperoxide according to claim 8, in which the secondary alkyl group-substituted methylbenzene is isopropyl xylene.

12. A process for preparing hydroperoxide according to claim 8, in which the secondary alkyl group-substituted methylbenzene is 3,5-dimethyl isopropyl benzene.

13. A process for preparing hydroperoxide according to claim 1, in which the water is used in an amount ranging from 0.01 to 20 parts and the metal chelate compound is used in an amount of 3 parts or less per 100 parts of the secondary alkyl group-substituted methylbenzene.

14. A process for preparing hydroperoxide according to claim 1, in which the water is used in an amount ranging from 0.1 to 2 parts and the metal chelate compound is used in an amount ranging from 0.001 to 1 part per 100 parts of the secondary alkyl group-substituted methylbenzene.

* * * * *